(12) United States Patent
Menges et al.

(10) Patent No.: US 10,212,934 B2
(45) Date of Patent: Feb. 26, 2019

(54) PESTICIDAL COMPOSITIONS

(71) Applicant: BASF AGRO B.V., Arnheim (NL)

(72) Inventors: Frederik Menges, Schriesheim (DE); Martin Semar, Gleiszellen-Gleishorbach (DE); Lutz Brahm, Worms (DE); Annette Schuster, Schifferstadt (DE); Florent Mazuir, Raleigh, NC (US)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 15/319,963

(22) PCT Filed: Jun. 15, 2015

(86) PCT No.: PCT/EP2015/063269
§ 371 (c)(1),
(2) Date: Dec. 19, 2016

(87) PCT Pub. No.: WO2015/197393
PCT Pub. Date: Dec. 30, 2015

(65) Prior Publication Data
US 2017/0127676 A1    May 11, 2017

(30) Foreign Application Priority Data
Jun. 25, 2014 (EP) .................... 14173980

(51) Int. Cl.
| A01N 43/653 | (2006.01) |
| A01N 25/00 | (2006.01) |
| A01N 25/08 | (2006.01) |
| A01N 43/40 | (2006.01) |
| A01N 43/80 | (2006.01) |
| A01N 43/90 | (2006.01) |
| A01N 47/22 | (2006.01) |
| A01N 47/24 | (2006.01) |

(52) U.S. Cl.
CPC .......... *A01N 43/653* (2013.01); *A01N 25/00* (2013.01); *A01N 25/08* (2013.01); *A01N 43/40* (2013.01); *A01N 43/80* (2013.01); *A01N 43/90* (2013.01); *A01N 47/22* (2013.01); *A01N 47/24* (2013.01)

(58) Field of Classification Search
CPC ....... A01N 43/653; A01N 43/40; A01N 43/48
See application file for complete search history.

(56) References Cited

U.S. PATENT DOCUMENTS

| 4,242,121 A | 12/1980 | Hawkins |
| 4,599,362 A | 7/1986 | Tachibana |
| 4,940,720 A | 7/1990 | Nevill et al. |
| 4,940,721 A | 7/1990 | Nevill et al. |
| 4,945,100 A | 7/1990 | Nyfeler et al. |
| 4,992,458 A | 2/1991 | Riebli |
| 5,143,932 A | 9/1992 | Dutzmann |
| 5,162,358 A | 11/1992 | Dehne |
| 8,492,312 B2 | 7/2013 | Thomas |
| 8,546,577 B2 | 10/2013 | Jeschke et al. |
| 2008/0108686 A1 | 5/2008 | Strathmann |
| 2009/0036509 A1 | 2/2009 | Grammenos |
| 2009/0286768 A1 | 11/2009 | Jin |
| 2010/0240619 A1 | 9/2010 | Gregory et al. |
| 2014/0012855 A1 | 1/2014 | Bingham |
| 2014/0127322 A1 | 5/2014 | Oberholzer et al. |
| 2015/0250173 A1 | 9/2015 | Braun |

FOREIGN PATENT DOCUMENTS

| AU | 611315 B2 | 6/1991 | |
| CA | 1100976 A1 | 5/1981 | |
| CA | 1187084 A1 | 5/1985 | |
| CA | 1209152 A1 | 8/1986 | |
| CA | 1210404 A1 | 8/1986 | |
| CN | 101225074 A | 7/2008 | |
| CS | 247200 B2 | 12/1986 | |
| DE | 2325878 A1 | 12/1974 | |
| DE | 3801233 A1 | 8/1988 | |
| DE | 3733755 A1 | 4/1989 | |
| DE | 4003180 A1 | 8/1991 | |
| EP | 0000017 A1 | 12/1978 | |
| EP | 0077479 A2 | 4/1983 | |
| EP | 0113640 A2 | 7/1984 | |
| EP | 0114567 A2 | 8/1984 | |
| EP | 0126430 | 11/1984 | |
| EP | 0275955 A1 | 7/1988 | |
| EP | 0354183 | 2/1990 | |
| EP | 354183 A2 | 2/1990 | |
| EP | 0440950 A2 | 8/1991 | |
| EP | 0470466 A2 | 2/1992 | |
| EP | 1431275 A1 | 6/2004 | |
| EP | 2559688 | 2/2013 | |
| EP | 2835052 | * 7/2014 | ............. A01N 43/54 |

(Continued)

OTHER PUBLICATIONS

International Search Report, issued in PCT/EP2015/063269, dated Sep. 15, 2015.
International Preliminary Report on Patentability, issued in PCT/EP2015/063269, dated Dec. 27, 2016.
Extended European Search Report, issued in EP Application No. 17178321.0, dated Oct. 11, 2017.
Extended European Search Report, issued in EP Application No. 17178393.9, dated Oct. 9, 2017.
Afon'Kin, A.A. et al. "Synthesis of Some Electron-Rich Aryl(hetaryl)oxarines under Phase-Transfer and Homogenous Conditions", Russian Journal of Organic Chemistry, 2008, p. 1776-1779, vol. 44, No. 12.
Akama, Tsutomu, et al. "Discovery and structure-activity study of a novel benzoxaborole anti-inflammatory agent. (AN2728) for the potential topical treatment of psoriasis and atopic dermatitis", Bioorganic & Medicinal Chemistry Letters, 2009, p. 2129-2132, vol. 19.

(Continued)

*Primary Examiner* — Sreenivasan Padmanabhan
*Assistant Examiner* — Danielle Sullivan
(74) *Attorney, Agent, or Firm* — Brinks Gilson & Lione

(57) ABSTRACT

The present invention relates to compositions comprising a triazole compound as component I and as a component II a compound selected from (II-1) to (II-8) and to the agrochemical compositions and the uses thereof.

13 Claims, No Drawings

(56) References Cited

FOREIGN PATENT DOCUMENTS

| | | | | |
|---|---|---|---|---|
| FR | 2491924 A1 | 4/1982 | | |
| GB | 2064520 A1 | 6/1981 | | |
| GB | 2132195 A1 | 7/1984 | | |
| GB | 2143815 A | * 2/1985 | ........... A01N 43/653 | |
| GB | 2143815 A1 | 2/1985 | | |
| JP | 59-222434 | 12/1984 | | |
| JP | 2-83304 | 3/1990 | | |
| NZ | 230176 A | 1/1992 | | |
| WO | 1996041804 | 12/1996 | | |
| WO | 02085891 A1 | 10/2002 | | |
| WO | 03064572 A1 | 8/2003 | | |
| WO | 2005123689 A1 | 12/2005 | | |
| WO | 2005123690 A1 | 12/2005 | | |
| WO | 2006015866 A1 | 2/2006 | | |
| WO | 2006087373 A1 | 8/2006 | | |
| WO | 2006109933 A1 | 10/2006 | | |
| WO | 2006119876 A1 | 11/2006 | | |
| WO | 2007031308 A2 | 3/2007 | | |
| WO | 2007115644 A1 | 10/2007 | | |
| WO | 2008082198 A1 | 7/2008 | | |
| WO | 2010146114 A1 | 12/2010 | | |
| WO | 2011099804 A2 | 8/2011 | | |
| WO | 2012035050 A2 | 3/2012 | | |
| WO | 2012037782 A1 | 3/2012 | | |
| WO | 2012090515 A1 | 7/2012 | | |
| WO | 2012092115 A1 | 7/2012 | | |
| WO | WO 2013007767 | 1/2013 | | |
| WO | WO 2013010862 | 1/2013 | | |
| WO | WO 2013010885 | 1/2013 | | |
| WO | WO 2013010894 | 1/2013 | | |
| WO | WO 2013024075 | 2/2013 | | |
| WO | WO 2013024076 | 2/2013 | | |
| WO | WO 2013024077 | 2/2013 | | |
| WO | WO 2013024080 | 2/2013 | | |
| WO | WO 2013024081 | 2/2013 | | |
| WO | WO 2013024082 | 2/2013 | | |
| WO | WO 2013024083 | 2/2013 | | |
| WO | WO 2014/079724 | * 5/2014 | ............. A01N 63/00 | |
| WO | WO 2014079719 | 5/2014 | | |
| WO | WO 2014079724 | 5/2014 | | |
| WO | WO 2014079728 | 5/2014 | | |
| WO | WO 2014079730 | 5/2014 | | |
| WO | WO 2014079752 | 5/2014 | | |
| WO | WO 2014079754 | 5/2014 | | |
| WO | WO 2014079764 | 5/2014 | | |
| WO | WO 2014079766 | 5/2014 | | |
| WO | WO 2014079769 | 5/2014 | | |
| WO | WO 2014079770 | 5/2014 | | |
| WO | WO 2014079771 | 5/2014 | | |
| WO | WO 2014079772 | 5/2014 | | |
| WO | WO 2014079773 | 5/2014 | | |
| WO | WO 2014079774 | 5/2014 | | |
| WO | WO 2014079804 | 5/2014 | | |
| WO | WO 2014079813 | 5/2014 | | |
| WO | WO 2014079814 | 5/2014 | | |
| WO | WO 2014079841 | 5/2014 | | |
| WO | WO 2014095932 | 6/2014 | | |
| WO | WO 2014095994 | 6/2014 | | |
| WO | WO 2015003908 | 1/2015 | | |
| WO | WO 2015113860 | 8/2015 | | |
| WO | WO 2015135701 | 9/2015 | | |
| WO | WO 2015169711 | 11/2015 | | |

OTHER PUBLICATIONS

Brandes, Bridget D., et al., "Synthesis of enantiopure 3-chlorostyrene oxide via an asymmetric epoxidation-hydrolytic kinetic resolution sequence", Tetrahedron; Asymmetry, 1997, p. 3927-3933, vol. 8, No. 23.

Forrester, Julie, et al. "Generation of trimethylsulfonium cation from dimethyl sulfoxide and dimethyl sulfate: implication s for the synthesis of epoxides from aldehydes and ketones", J. Chem. Soc. Perkin Trans. 1, 1995, pp. 2289-2291, vol. 1995.

Kuzenkov, A.V., "Synthesis of substituted 2-azoloy1-1-pyridylethan-1-ols", Chemistry of hererocyclic compounds, 2003, p. 1492-1495 vol. 39, No. 11.

Lima, Lidia Moreira et al., "Bioisosterism: A useful strategy for molecular Modification and drug design", Current Medicinal Chemistry, 2005, p. 23-49, vol. 12.

Mosset, Paul et al. "Trimethylsulfonium Methylsulfate, a simple and efficient epoxidizing agent", Synthetic Communications, 1985, p. 749-757, vol. 15, No. 8.

Office Action, issued in co-pending U.S. Appl. No. 14/653,578, dated Aug. 24, 2016.

Final Office Action, issued in co-pending U.S. Appl. No. 14/653,578, dated Apr. 28, 2017.

Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.

Office Action, issued in co-pending U.S. Appl. No. 14/653,578, dated Oct. 24, 2017.

Office Action, issued in co-pending U.S. Appl. No. 14/902,877, dated Mar. 8, 2018.

* cited by examiner

PESTICIDAL COMPOSITIONS

This application is a National Stage application of International Application No. PCT/EP2015/063269, filed Jun. 15, 2015. This application also claims priority under 35 U.S.C. § 119 to European Patent Application No. 14173980.5, filed Jun. 25, 2014.

The present invention relates to compositions comprising,
1) as component I a compound selected from:
compound I-1 2-[2-chloro-4-(4-chlorophenoxy)phenyl]-1-(1,2,4-triazol-1-yl)pent-3-yn-2-ol;
compound I-2 1-[2-chloro-4-(4-chlorophenoxy)phenyl]-1-cyclopropyl-2-(1,2,4-triazol-1-yl)ethanol;
compound I-3 2-[4-(4-chlorophenoxy)-2-(trifluoromethyl)phenyl]-1-(1,2,4-triazol-1-yl)propan-2-ol;
compound I-4 1-[4-(4-chlorophenoxy)-2-(trifluoromethyl)phenyl]-1-cyclopropyl-2-(1,2,4-triazol-1-yl)ethanol;
compound I-5 2-[4-(4-chlorophenoxy)-2-(trifluoromethyl)phenyl]-3-methyl-1-(1,2,4-triazol-1-yl)butan-2-ol;
compound I-6 1-[2-[2-chloro-4-(4-chlorophenoxy)phenyl]-2-methoxy-pent-3-ynyl]-1,2,4-triazole;
compound I-7 2-[4-(4-chlorophenoxy)-2-(trifluoromethyl)phenyl]-1-(1,2,4-triazol-1-yl)butan-2-ol;
compound I-8 1-[2-[2-chloro-4-(4-chlorophenoxy)phenyl]-2-cyclopropyl-2-methoxy-ethyl]-1,2,4-triazole;
compound I-9 1-[2-[4-(4-chlorophenoxy)-2-(trifluoromethyl)phenyl]-2-methoxy-propyl]-1,2,4-triazole;
compound I-10 2-[2-chloro-4-(4-chlorophenoxy)phenyl]-3,3-dimethyl-1-(1,2,4-triazol-1-yl)butan-2-ol,
compound I-11 1-[2-[4-(4-chlorophenoxy)-2-(trifluoromethyl)phenyl]-2-cyclopropyl-2-methoxy-ethyl]-1,2,4-triazole;
compound I-12 1-[2-[2-chloro-4-(4-chlorophenoxy)phenyl]-2-methoxy-3,3-dimethyl-butyl]-1,2,4-triazole;
compound I-13 1-[2-[4-(4-chlorophenoxy)-2-(trifluoromethyl)phenyl]-2-methoxy-butyl]1,2,4-triazole;
compound I-14 2-[4-(4-chlorophenoxy)-2-(trifluoromethyl)phenyl]-1-(1,2,4-triazol-1-yl)pent-3-yn-2-ol;
compound I-15 1-[2-[4-(4-chlorophenoxy)-2-(trifluoromethyl)phenyl]-2-methoxy-pent-3-ynyl]-1,2,4-triazole;
compound I-16 2-[4-(4-chlorophenoxy)-2-(trifluoromethyl)phenyl]-1-(1,2,4-triazol-1-yl)but-3-yn-2-ol;
compound I-17 2-[2-chloro-4-(4-chlorophenoxy)phenyl]-1-(1,2,4-triazol-1-yl)propan-2-ol;
compound I-18 2-[2-chloro-4-(4-fluorophenoxy)phenyl]-1-(1,2,4-triazol-1-yl)propan-2-ol;
compound I-19 2-[2-chloro-4-(4-chlorophenoxy)phenyl]-3-methyl-1-(1,2,4-triazol-1-yl)butan-2-ol;
compound I-20 1-[2-[2-chloro-4-(4-chlorophenoxy)phenyl]-2-methoxy-propyl]-1,2,4-triazole;
compound I-21 1-[2-[2-chloro-4-(4-chlorophenoxy)phenyl]-2-methoxy-butyl]-1,2,4-triazole;
compound I-22 1-[2-[2-chloro-4-(4-chlorophenoxy)phenyl]-2-methoxy-pentyl]-1,2,4-triazole;
compound I-23 2-[2-chloro-4-(4-chlorophenoxy)phenyl]-1,1,1-trifluoro-3-(1,2,4-triazol-1-yl)propan-2-ol;
compound I-24 2-[2-chloro-4-(4-chlorophenoxy)phenyl]-3-fluoro-1-(1,2,4-triazol-1-yl)butan-2-ol hydrochloride;
compound I-25 2-[2-chloro-4-(4-chlorophenoxy)phenyl]-1-(1,2,4-triazol-1-yl)pent-4-yn-2-ol;
compound I-26 2-[2-chloro-4-(4-chlorophenoxy)phenyl]-1-methoxy-3-(1,2,4-triazol-1-yl)propan-2-ol;
compound I-27 2-[2-chloro-4-(4-fluorophenoxy)phenyl]-1-methoxy-3-(1,2,4-triazol-1-yl)propan-2-ol;
compound I-28 2-[4-(4-chlorophenoxy)-2-(trifluoromethyl)phenyl]-1-(1,2,4-triazol-1-yl)pentan-2-ol;
compound I-29 and 2-[4-(4-fluorophenoxy)-2-(trifluoromethyl)phenyl]-1-(1,2,4-triazol-1-yl)propan-2-ol;
compound I-30 2-[2-chloro-4-(4-chlorophenoxy)phenyl]-1-(1,2,4-triazol-1-yl)butan-2-ol; and
compound I-31 2-[2-chloro-4-(4-chlorophenoxy)phenyl]-1-(1,2,4-triazol-1-yl)pentan-2-ol;
and
2) as component II a compound selected from the group of
oxathiapiprolin (II-1); triadimenol (II-2); sulfoxaflor (II-3); methiocarb (II-4); cypermethrin (II-5); thiodicarb (II-6); triflumezopyrim (mesoionic) (II-7) and flupyradifurone (II-8).

In particular, the present invention relates to compositions comprising,
1) as component I a compound selected from:
compound I-1 2-[2-chloro-4-(4-chlorophenoxy)phenyl]-1-(1,2,4-triazol-1-yl)pent-3-yn-2-ol;
compound I-2 1-[2-chloro-4-(4-chlorophenoxy)phenyl]-1-cyclopropyl-2-(1,2,4-triazol-1-yl)ethanol;
compound I-3 2-[4-(4-chlorophenoxy)-2-(trifluoromethyl)phenyl]-1-(1,2,4-triazol-1-yl)propan-2-ol;
compound I-4 1-[4-(4-chlorophenoxy)-2-(trifluoromethyl)phenyl]-1-cyclopropyl-2-(1,2,4-triazol-1-yl)ethanol;
compound I-5 2-[4-(4-chlorophenoxy)-2-(trifluoromethyl)phenyl]-3-methyl-1-(1,2,4-triazol-1-yl)butan-2-ol;
and
2) as component II a compound selected from the group of
oxathiapiprolin (II-1); triadimenol (II-2); sulfoxaflor (II-3); methiocarb (II-4); cypermethrin (II-5); thiodicarb (II-6); triflumezopyrim (mesoionic) (II-7) and flupyradifurone (II-8).

The invention furthermore relates to the use of the inventive compositions as pesticides in particular for controlling phytopathogenic fungi as detailed herein and preparations or compositions comprising them. The invention furthermore also relates to seed comprising the compositions. The invention furthermore also relates to methods for controlling pests, in particular phytopathogenic fungi as detailed herein, wherein the fungi or the materials, plants, the soil or seed to be protected from fungal attack are treated with an effective amount of a compositions according to the invention. The invention furthermore also relates to processes for preparing the compositions according to the invention.

With a view to reducing the application rates and broadening the activity spectrum of the known compounds, it was an object of the present invention to provide compositions which, at a reduced total amount of active compounds applied, show improved activity against important pests, in particular phythopathogenic fungi, in particular for certain indications. It was a further object to provide for compositions that are useful for the control of specific pathogens in specific important crops that are often susceptible to the attack of pathogens.

Accordingly we have found the compositions and uses defined at the outset and in the following description.

The compounds I (component I) can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2). Furthermore, compounds I (component I), its preparation and use in crop protection are described in WO 2013/007767 (PCT/EP2012/063626), WO 2013/024076 (PCT/EP2012/065835), WO 2013/024075 (PCT/EP2012/065834),), WO 2013/024077 (PCT/EP2012/065836), WO 2013/024081 (PCT/EP2012/065848), WO 2013/024080 (PCT/EP2012/

065847), WO 2013/024083 (PCT/EP2012/065852) WO 2013/010862 (PCT/EP2012/063526), WO 2013/010894 (PCT/EP2012/063635), WO 2013/010885 (PCT/EP2012/063620), WO 2013/024082 (PCT/EP2012/065850), which also disclose certain compositions with other active compounds. Owing to the basic character of their nitrogen atoms, the component I, i.e in particular compound I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31 or any group of compounds I detailed above, is capable of forming salts or adducts with inorganic or organic acids or with metal ions, in particular salts with inorganic acids.

I-1

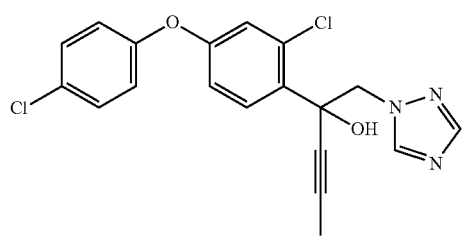

2-[2-chloro-4-(4-chlorophenoxy)phenyl]-1-(1,2,4-triazol-1-yl)pent-3-yn-2-ol

I-2

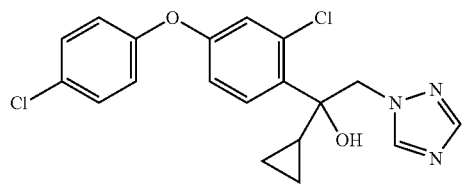

1-[2-chloro-4-(4-chlorophenoxy)phenyl]-1-cyclopropyl-2-(1,2,4-triazol-1-yl)ethanol

I-3

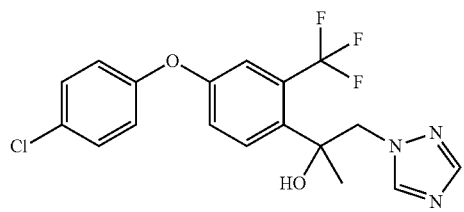 [SMILES: CC(O)(Cn1cncn1)c1ccc(Oc2ccc(Cl)cc2)cc1C(F)(F)F]

2-[4-(4-chlorophenoxy)-2-(trifluoromethyl)phenyl]-1-(1,2,4-triazol-1-yl)propan-2-ol

I-4

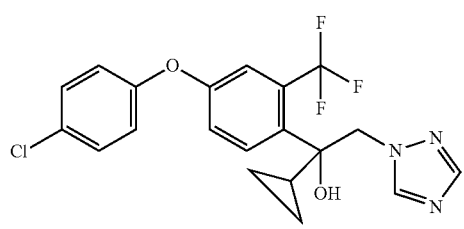

1-[4-(4-chlorophenoxy)-2-(trifluoromethyl)phenyl]-1-cyclopropyl-2-(1,2,4-triazol-1-yl)ethanol

I-5

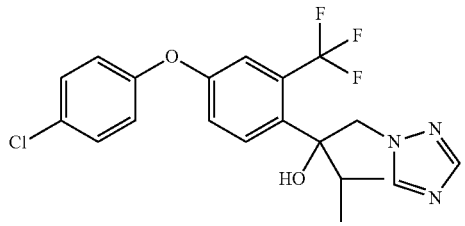

2-[4-(4-chlorophenoxy)-2-(trifluoromethyl)phenyl]-3-methyl-1-(1,2,4-triazol-1-yl)butan-2-ol

I-6

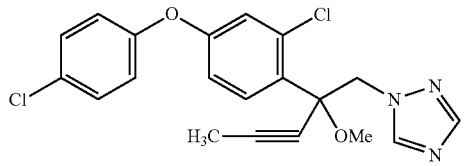

1-[2-[2-chloro-4-(4-chlorophenoxy)phenyl]-2-methoxy-pent-3-ynyl]-1,2,4-triazole

I-7

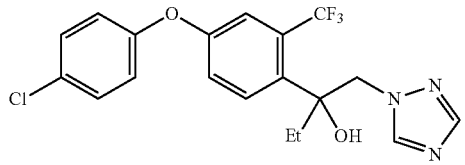

2-[4-(4-chlorophenoxy)-2-(trifluoromethyl)phenyl]-1-(1,2,4-triazol-1-yl)butan-2-ol

I-8

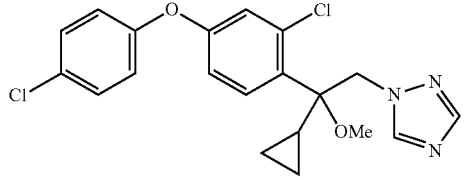

1-[2-[2-chloro-4-(4-chlorophenoxy)phenyl]-2-cyclopropyl-2-methoxy-ethyl]-1,2,3,4-triazole

I-9

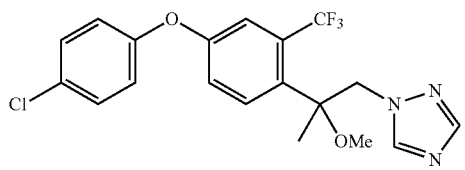

1-[2-[4-(4-chlorophenoxy)-2-(trifluoromethyl)phenyl]-2-methoxy-propyl]-1,2,4-triazole

I-10

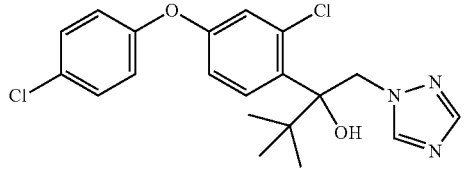

2-[2-chloro-4-(4-chlorophenoxy)phenyl]-3,3-dimethyl-1-(1,2,4-triazol-1-yl)butan-2-ol -continued

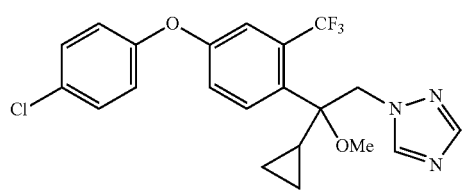

1-[2-[4-(4-chlorophenoxy)-2-(trifluoromethyl)phenyl]-2-cyclopropyl-2-methoxy-ethyl]-1,2,4-triazole

I-11

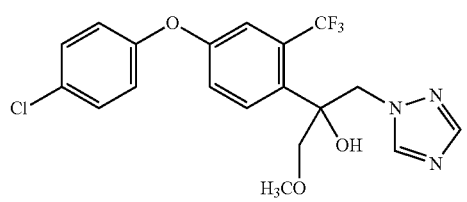

2-[2-trifluoromethyl-4-(4-chlorophenoxy)phenyl]-1-methoxy-3-(1,2,4-triazol-1-yl)propan-2-ol

I-12

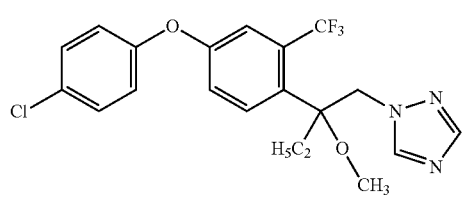

1-[2-[4-(4-chlorophenoxy)-2-(trifluoromethyl)phenyl]-2-methoxy-butyl]1,2,4-triazole

I-13

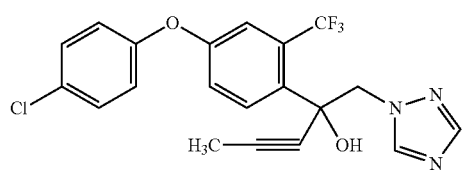

2-[4-(4-chlorophenoxy)-2-(trifluoromethyl)phenyl]-1-(1,2,4-triazol-1-yl)pent-3-yn-2-ol

I-14

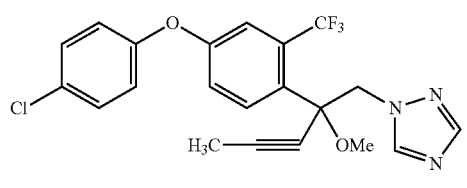

1-[2-[4-(4-chlorophenoxy)-2-(trifluoromethyl)phenyl]-2-methoxy-pent-3-ynyl]-1,2,4-triazole

I-15

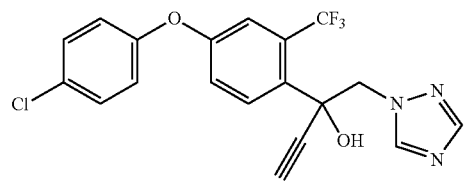

2-[4-(4-chlorophenoxy)-2-(trifluoromethyl)phenyl]-1-(1,2,4-triazol-1-yl)but-3-yn-2-ol

I-16

-continued

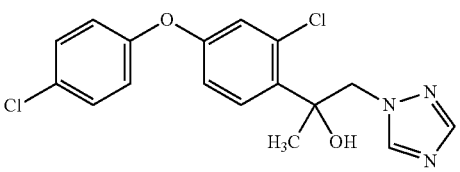

2-[2-chloro-4-(4-chlorophenoxy)phenyl]-1-(1,2,4-triazol-1-yl)propan-2-ol

I-17

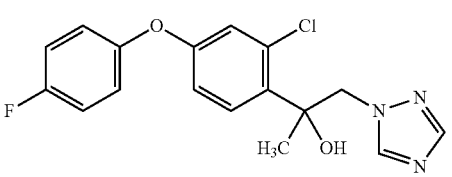

2-[2-chloro-4-(4-fluorophenoxy)phenyl]-1-(1,2,4-triazol-1-yl)propan-2-ol

I-18

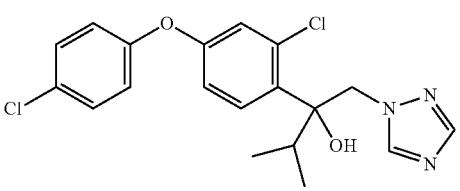

2-[2-chloro-4-(4-chlorophenoxy)phenyl]-3-methyl-1-(1,2,4-triazol-1-yl)butan-2-ol

I-19

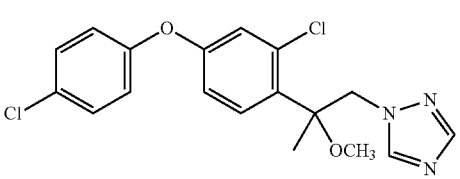

1-[2-[2-chloro-4-(4-chlorophenoxy)phenyl]-2-methoxy-propyl]-1,2,4-triazole

I-20

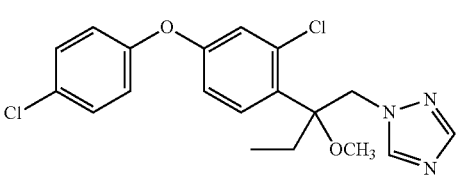

1-[2-[2-chloro-4-(4-chlorophenoxy)phenyl]-2-methoxy-butyl]-1,2,4-triazole

I-21

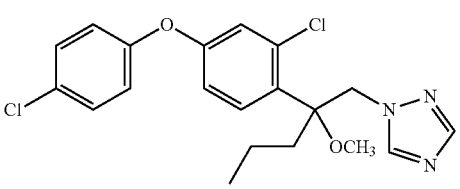

1-[2-[2-chloro-4-(4-chlorophenoxy)phenyl]-2-methoxy-pentyl]-1,2,4-triazole

I-22

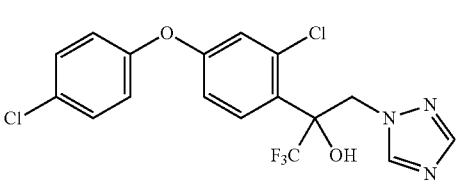

2-[2-chloro-4-(4-chlorophenoxy)phenyl]-1,1,1-trifluoro-3-(1,2,4-triazol-1-yl)propan-2-ol

I-23

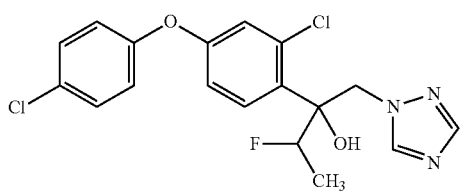

2-[2-chloro-4-(4-chlorophenoxy)phenyl]-3-fluoro-1-
(1,2,4-triazol-1-yl)butan-2-ol hydrochloride

I-24

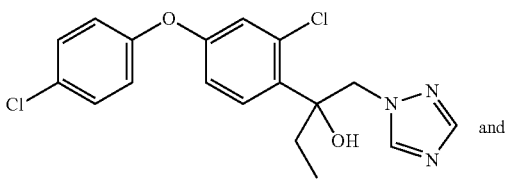

2-[2-chloro-4-(4-chlorophenoxy)phenyl]-1-
(1,2,4-triazol-1-yl)butan-2-ol and

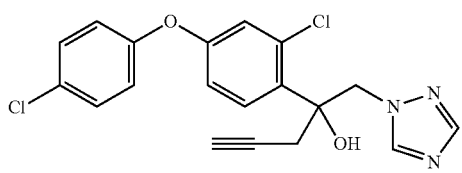

2-[2-chloro-4-(4-chlorophenoxy)phenyl]-1-
(1,2,4-triazol-1-yl)pent-4-yn-2-ol

I-25

I-31

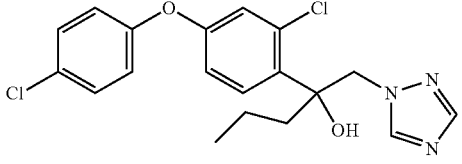

2-[2-chloro-4-(4-chlorophenoxy)phenyl]-1-
(1,2,4-triazol-1-yl)pentan-2-ol

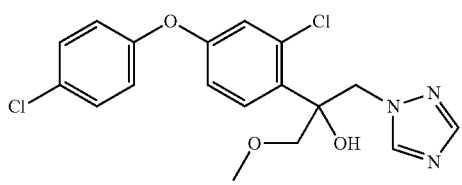

2-[2-chloro-4-(4-chlorophenoxy)phenyl]-1-
methoxy-3-(1,2,4-triazol-1-yl)propan-2-ol

I-26

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid and other arylcarboxylic acids, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid etc. Suitable metal ions are in particular the ions of the elements of the second main group, in particular calcium and magnesium, of the third and fourth main group, in particular aluminum, tin and lead, and also of the elements of transition groups one to eight, in particular chromium, manganese, iron, cobalt, nickel, copper, zinc, and others. Particular preference is given to the metal ions of the elements of transition groups of the fourth period. The metals can be present in the various valencies that they can assume.

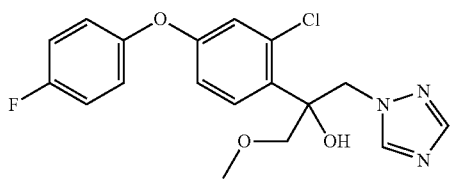

2-[2-chloro-4-(4-fluorophenoxy)phenyl]-1-
methoxy-3-(1,2,4-triazol-1-yl)propan-2-ol

I-27

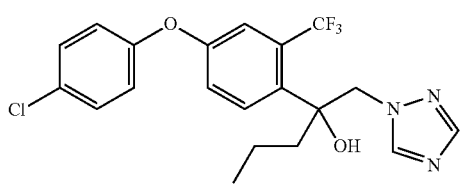

2-[4-(4-chlorophenoxy)-2-(trifluoromethyl)phenyl]-1-
(1,2,4-triazol-1-yl)pentan-2-ol

I-28

Components I comprise chiral centers and they are generally obtained in the form of racemates. The R- and S-enantiomers of the compounds according to the invention can be separated and isolated in pure form with methods known by the skilled person, e.g. by using chiral HPLC. Suitable for use as antimicrobial agents are both the enantiomers and compositions thereof. This applies correspondingly to the compositions. Furthermore, components I can be present in different crystal modifications, which may differ in biological activity.

In particular, in each case, a racemic composition is present. Furthermore, any other proportions of the (R)-

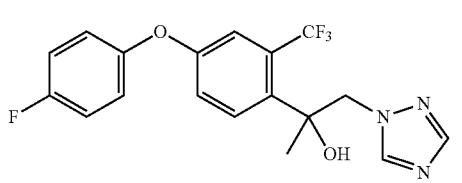

2-[4-(4-fluorophenoxy)-2-(trifluoromethyl)phenyl]-1-
(1,2,4-triazol-1-yl)propan-2-ol

I-29 enantiomer and the (S)-enantiomer may be present according to the present invention. This applies to every composition detailed herein.

According to one embodiment of the present invention, component I is compound I-1. Compound I-1 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-1.

According to one specific embodiment, the compound I-1 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-1 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-1: (R)-2-[2-chloro-4-(4-chlorophenoxy)phenyl]-1-(1,2,4-triazol-1-yl)pent-3-yn-2-ol; Compound (S)-I-1: (S)-2-[2-chloro-4-(4-chlorophenoxy)phenyl]-1-(1,2,4-triazol-1-yl)pent-3-yn-2-ol. According to a further embodiment of the present invention, component I is compound I-2. Compound I-2 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-2.

According to one specific embodiment, the compound I-2 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-2 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-2: (R)-1-[2-chloro-4-(4-chlorophenoxy)phenyl]-1-cyclopropyl-2-(1,2,4-triazol-1-yl)ethanol; compound (S)-I-2: (S)-1-[2-chloro-4-(4-chlorophenoxy)phenyl]-1-cyclopropyl-2-(1,2,4-triazol-1-yl)ethanol.

According to still a further embodiment of the present invention, component I is compound I-3. Compound I-3 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-3.

According to one specific embodiment, the compound I-3 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-3 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-3: (R)-2-[4-(4-chlorophenoxy)-2-(trifluoromethyl)phenyl]-1-(1,2,4-triazol-1-yl)propan-2-ol; compound (S)-I-3: (S)-2-[4-(4-chlorophenoxy)-2-(trifluoromethyl)phenyl]-1-(1,2,4-triazol-1-yl)propan-2-ol.

According to still a further embodiment of the present invention, component I is compound I-4. Compound I-4 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-4.

According to one specific embodiment, the compound I-4 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-4 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-4: (R)-1-[4-(4-chlorophenoxy)-2-(trifluoromethyl)phenyl]-1-cyclopropyl-2-(1,2,4-triazol-1-yl)ethanol; compound (S)-I-4: (S)-1-[4-(4-chlorophenoxy)-2-(trifluoromethyl)phenyl]-1-cyclopropyl-2-(1,2,4-triazol-1-yl)ethanol.

According to still a further embodiment of the present invention, component I is compound I-5. Compound I-5 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-5.

According to one specific embodiment, the compound I-5 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-5 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-5: (R)-2-[4-(4-chlorophenoxy)-2-(trifluoromethyl)phenyl]-3-methyl-1-(1,2,4-triazol-1-yl)butan-2-ol; compound (S)-I-5: (S)-2-[4-(4-chlorophenoxy)-2-(trifluoromethyl)phenyl]-3-methyl-1-(1,2,4-triazol-1-yl)butan-2-ol.

According to still a further embodiment of the present invention, component I is compound I-6. Compound I-6 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-6.

According to one specific embodiment, the compound I-6 is provided and used as (R)-enantiomer with an enantomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-6 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-6: (S)-1-[2-[2-chloro-4-(4-chlorophenoxy)phenyl]-2-methoxy-pent-3-ynyl]-1,2,4-triazole; compound (R)-I-6: (R)-1-[2-[2-chloro-4-(4-chlorophenoxy)phenyl]-2-methoxy-pent-3-ynyl]-1,2,4-triazole.

According to still a further embodiment of the present invention, component I is compound I-7. Compound I-7 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-7.

According to one specific embodiment, the compound I-7 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-7 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

compound (S)-I-7: (S)-2-[4-(4-chlorophenoxy)-2-(trifluoromethyl)phenyl]-1-(1,2,4-triazol-1-yl)butan-2-ol; compound (R)-I-7: (R)-2-[4-(4-chlorophenoxy)-2-(trifluoromethyl)phenyl]-1-(1,2,4-triazol-1-yl)butan-2-ol.

According to still a further embodiment of the present invention, component I is compound I-8. Compound I-8 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-8.

According to one specific embodiment, the compound I-8 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-8 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-8: (S)-1-[2-[2-chloro-4-(4-chlorophenoxy)phenyl]-2-cyclopropyl-2-methoxy-ethyl]-1,2,4-triazole; Compound (R)-I-8: (R)-1-[2-[2-chloro-4-(4-chlorophenoxy)phenyl]-2-cyclopropyl-2-methoxy-ethyl]-1,2,4-triazole.

According to still a further embodiment of the present invention, component I is compound I-9. Compound I-9 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-9.

According to one specific embodiment, the compound I-9 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-9 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-9: (S)-1-[2-[4-(4-chlorophenoxy)-2-(trifluoromethyl)phenyl]-2-methoxy-propyl]-1,2,4-triazole; compound (R)-I-9: (R)-1-[2-[4-(4-chlorophenoxy)-2-(trifluoromethyl)phenyl]-2-methoxy-propyl]-1,2,4-triazole.

According to still a further embodiment of the present invention, component I is compound I-10. Compound I-10 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-10.

According to one specific embodiment, the compound I-10 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-10 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-10: (S)-2-[2-chloro-4-(4-chlorophenoxy)phenyl]-3,3-dimethyl-1-(1,2,4-triazol-1-yl)butan-2-ol; compound (R)-I-10: (R)-2-[2-chloro-4-(4-chlorophenoxy)phenyl]-3,3-dimethyl-1-(1,2,4-triazol-1-yl)butan-2-ol.

According to still a further embodiment of the present invention, component I is compound I-11. Compound I-11 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-11.

According to one specific embodiment, the compound I-11 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-11 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-11: (S)-1-[2-[4-(4-chlorophenoxy)-2-(trifluoromethyl)phenyl]-2-cyclopropyl-2-methoxy-ethyl]-1,2,4-triazole; compound (R)-I-11: (R)-1-[2-[4-(4-chlorophenoxy)-2-(trifluoromethyl)phenyl]-2-cyclopropyl-2-methoxy-ethyl]-1,2,4-triazole.

According to still a further embodiment of the present invention, component I is compound I-12. Compound I-12 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-12.

According to one specific embodiment, the compound I-12 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-12 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-12: (S)-2-[2-trifluoromethyl-4-(4-chlorophenoxy)phenyl]-1-methoxy-3-(1,2,4-triazol-1-yl)propan-2-ol; compound (R)-I-12: (R)-2-[2-trifluoromethyl-4-(4-chlorophenoxy)phenyl]-1-methoxy-3-(1,2,4-triazol-1-yl)propan-2-ol.

According to still a further embodiment of the present invention, component I is compound I-13. Compound I-13 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-13.

According to one specific embodiment, the compound I-13 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-13 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-13: (S)-1-[2-[4-(4-chlorophenoxy)-2-(trifluoromethyl)phenyl]-2-methoxy-butyl]1,2,4-triazole; Compound (R)-I-13: (R)-1-[2-[4-(4-chlorophenoxy)-2-(trifluoromethyl)phenyl]-2-methoxy-butyl]1,2,4-triazole.

According to still a further embodiment of the present invention, component I is compound I-14. Compound I-14 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-14.

According to one specific embodiment, the compound I-14 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-14 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-14: (S)-2-[4-(4-chlorophenoxy)-2-(trifluoromethyl)phenyl]-1-(1,2,4-triazol-1-yl)pent-3-yn-2-ol; compound (R)-I-14: (R)-2-[4-(4-chlorophenoxy)-2-(trifluoromethyl)phenyl]-1-(1,2,4-triazol-1-yl)pent-3-yn-2-ol.

According to still a further embodiment of the present invention, component I is compound I-15. Compound I-15 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-15.

According to one specific embodiment, the compound I-15 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-15 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-15: (S)-1-[2-[4-(4-chlorophenoxy)-2-(trifluoromethyl)phenyl]-2-methoxy-pent-3-ynyl]-1,2,4-triazole; Compound (R)-I-15: (R)-1-[2-[4-(4-chlorophenoxy)-2-(trifluoromethyl)phenyl]-2-methoxy-pent-3-ynyl]-1,2,4-triazole.

According to still a further embodiment of the present invention, component I is compound I-16. Compound I-16 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-16.

According to one specific embodiment, the compound I-16 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-16 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-16: (S)-2-[4-(4-chlorophenoxy)-2-(trifluoromethyl)phenyl]-1-(1,2,4-triazol-1-yl)but-3-yn-2-ol; compound (R)-I-16: (R)-2-[4-(4-chlorophenoxy)-2-(trifluoromethyl)phenyl]-1-(1,2,4-triazol-1-yl)but-3-yn-2-ol.

According to one embodiment of the present invention, component I is compound I-17. Compound I-17 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-17.

According to one specific embodiment, the compound I-17 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-17 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-17: (R)-12-[2-chloro-4-(4-chlorophenoxy)phenyl]-1-(1,2,4-triazol-1-yl)propan-2-ol; compound (S)-I-4: (S)-12-[2-chloro-4-(4-chlorophenoxy)phenyl]-1-(1,2,4-triazol-1-yl)propan-2-ol.

According to a further embodiment of the present invention, component I is compound I-18. Compound I-18 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-18.

According to one specific embodiment, the compound I-18 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-18 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-18: (S)-2-[2-chloro-4-(4-fluorophenoxy)phenyl]-1-(1,2,4-triazol-1-yl)propan-2-ol; Compound (R)-I-18: (R)-2-[2-chloro-4-(4-fluorophenoxy)phenyl]-1-(1,2,4-triazol-1-yl)propan-2-ol.

According to still a further embodiment of the present invention, component I is compound I-19. Compound I-19 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-19.

According to one specific embodiment, the compound I-19 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-19 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compounds (S)-I-19: (S)-2-[2-chloro-4-(4-chlorophenoxy)phenyl]-3-methyl-1-(1,2,4-triazol-1-yl)butan-2-ol; Compounds (R)-I-19: (R)-2-[2-chloro-4-(4-chlorophenoxy)phenyl]-3-methyl-1-(1,2,4-triazol-1-yl)butan-2-ol.

According to still a further embodiment of the present invention, component I is compound I-20. Compound I-20 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-20.

According to one specific embodiment, the compound I-20 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-20 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-20: (S)-1-[2-[2-chloro-4-(4-chlorophenoxy)phenyl]-2-methoxy-propyl]-1,2,4-triazole; Compound (R)-I-20: (R)-1-[2-[2-chloro-4-(4-chlorophenoxy)phenyl]-2-methoxy-propyl]-1,2,4-triazole.

According to still a further embodiment of the present invention, component I is compound I-21. Compound I-21 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-21.

According to one specific embodiment, the compound I-21 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-21 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-21: (S)-1-[2-[2-chloro-4-(4-chlorophenoxy)phenyl]-2-methoxy-butyl]-1,2,4-triazole; Compound (R)-I-21: (R)-1-[2-[2-chloro-4-(4-chlorophenoxy)phenyl]-2-methoxy-butyl]-1,2,4-triazole.

According to still a further embodiment of the present invention, component I is compound I-22. Compound I-22 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-22.

According to one specific embodiment, the compound I-22 is provided and used as (R)-enantiomer with an enantomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-22 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-22: (S)-1-[2-[2-chloro-4-(4-chlorophenoxy)phenyl]-2-methoxy-pentyl]-1,2,4-triazole; Compound (R)-I-22: (R)-1-[2-[2-chloro-4-(4-chlorophenoxy)phenyl]-2-methoxy-pentyl]-1,2,4-triazole.

According to still a further embodiment of the present invention, component I is compound I-23. Compound I-23 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-23.

According to one specific embodiment, the compound I-23 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-23 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-23: (S)-2-[2-chloro-4-(4-chlorophenoxy)phenyl]-1,1,1-trifluoro-3-(1,2,4-triazol-1-yl)propan-2-ol; Compound (R)-I-23: (R)-2-[2-chloro-4-(4-chlorophenoxy)phenyl]-1,1,1-trifluoro-3-(1,2,4-triazol-1-yl)propan-2-ol.

According to still a further embodiment of the present invention, component I is compound I-24. Compound I-24 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-24.

According to one specific embodiment, the compound I-24 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-24 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-24: (S)-2-[2-chloro-4-(4-chlorophenoxy)phenyl]-3-fluoro-1-(1,2,4-triazol-1-yl)butan-2-ol hydrochloride; Compound (R)-I-24: (R)-2-[2-chloro-4-(4-chlorophenoxy)phenyl]-3-fluoro-1-(1,2,4-triazol-1-yl)butan-2-ol hydrochloride.

According to still a further embodiment of the present invention, component I is compound I-25. Compound I-25 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-25.

According to one specific embodiment, the compound I-25 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-25 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-25: (S)-2-[2-chloro-4-(4-chlorophenoxy)phenyl]-1-(1,2,4-triazol-1-yl)pent-4-yn-2-ol; Compound (R)-I-25: (R)-2-[2-chloro-4-(4-chlorophenoxy)phenyl]-1-(1,2,4-triazol-1-yl)pent-4-yn-2-ol.

According to still a further embodiment of the present invention, component I is compound I-26. Compound I-26 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-26.

According to one specific embodiment, the compound I-26 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-26 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-26: (S)-2-[2-chloro-4-(4-chlorophenoxy)phenyl]-1-methoxy-3-(1,2,4-triazol-1-yl)propan-2-ol; Compound (R)-I-26: (R)-2-[2-chloro-4-(4-chlorophenoxy)phenyl]-1-methoxy-3-(1,2,4-triazol-1-yl)propan-2-ol.

According to still a further embodiment of the present invention, component I is compound I-27. Compound I-27 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-27.

According to one specific embodiment, the compound I-27 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-27 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-27: (S)-2-[2-chloro-4-(4-fluorophenoxy)phenyl]-1-methoxy-3-(1,2,4-triazol-1-yl)propan-2-ol; Compound (R)-I-27: (R)-2-[2-chloro-4-(4-fluorophenoxy)phenyl]-1-methoxy-3-(1,2,4-triazol-1-yl)propan-2-ol.

According to still a further embodiment of the present invention, component I is compound I-28. Compound I-28 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-28.

According to one specific embodiment, the compound I-28 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-28 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-28: (S)-2-[4-(4-chlorophenoxy)-2-(trifluoromethyl)phenyl]-1-(1,2,4-triazol-1-yl)pentan-2-ol; Compound (R)-I-28: (R)-2-[4-(4-chlorophenoxy)-2-(trifluoromethyl)phenyl]-1-(1,2,4-triazol-1-yl)pentan-2-ol.

According to still a further embodiment of the present invention, component I is compound I-29. Compound I-29 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-29.

According to one specific embodiment, the compound I-29 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-29 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-29: (S)-2-[4-(4-fluorophenoxy)-2-(trifluoromethyl)phenyl]-1-(1,2,4-triazol-1-yl)propan-2-ol;
Compound (R)-I-29: (R)-2-[4-(4-fluorophenoxy)-2-(trifluoromethyl)phenyl]-1-(1,2,4-triazol-1-yl)propan-2-ol.

According to still a further embodiment of the present invention, component I is compound I-30. Compound I-30 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-30.

According to one specific embodiment, the compound I-30 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-30 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-30: (S)-2-[2-chloro-4-(4-chlorophenoxy)phenyl]-1-(1,2,4-triazol-1-yl)butan-2-ol; Compound (R)-I-30: (R)-2-[2-chloro-4-(4-chlorophenoxy)phenyl]-1-(1,2,4-triazol-1-yl)butan-2-ol.

According to still a further embodiment of the present invention, component I is compound I-31. Compound I-31 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-31.

According to one specific embodiment, the compound I-31 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-31 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-31: (S)-2-[2-chloro-4-(4-chlorophenoxy)phenyl]-1-(1,2,4-triazol-1-yl)pentan-2-ol; Compound (R)-I-31: (R)-2-[2-chloro-4-(4-chlorophenoxy)phenyl]-1-(1,2,4-triazol-1-yl)pentan-2-ol.

According to one further embodiment of the present invention, component I is selected from compounds I-1, I-2, I-3, I-4, I-5, I-6, I-7, I-8, I-9, I-11, I-13, I-14, I-15 and I-16. According to a more particular embodiment of the present invention, component I is selected from compounds I-1, I-2, I-6 and I-8. According to another more particular embodiment of the present invention, component I is selected from compounds I-3, I-4, I-5, I-7, I-9, I-11, I-13, I-14, I-15 and I-16.

According to still a further embodiment of the present invention, component I is selected from compounds I-1, I-2, I-3, I-4 and I-5, more specifically selected from I-1, I-3, I-4 and I-5. According to still a further embodiment of the present invention, component I is selected from compounds I-3, I-4 and I-5.

The preparation of component II and their action against harmful fungi are known (cf.: http://www.alanwood.net/pesticides/) and they are generally commercially available. Commercially available active compounds can be found, for example, in The Pesticide Manual, 14th Edition, British Crop Protection Council (2006) and other publications.

oxathiapiprolin (II-1): 1-(4-{4-[(5 RS)-5-(2,6-difluorophenyl)-4,5-dihydro-1,2-oxazol-3-yl]-1,3-thiazol-2-yl}-1-piperidyl)-2-[5-methyl-3-(trifluoromethyl)-1H-pyrazol-1-yl]ethanone triadimenol (II-2): (1 RS,2 RS;1 RS,2 SR)-1-(4-chlorophenoxy)-3,3-dimethyl-1-(1H-1,2,4-triazol-1-yl)butan-2-ol sulfoxaflor (II-3): [methyl(oxo){1-[6-(trifluoromethyl)-3-pyridyl]ethyl}-$\Lambda^6$-sulfanylidene]cyanamide methiocarb (II-4): 4-methylthio-3,5-xylyl methylcarbamate cypermethrin (II-5): (RS)-α-cyano-3-phenoxybenzyl (1 RS,3 RS;1 RS,3 SR)-3-(2,2-dichlorovinyl)-2,2-dimethylcyclopropanecarboxylate or (RS)-α-cyano-3-phenoxybenzyl (1 RS)-cis-trans-3-(2,2-dichlorovinyl)-2,2-dimethylcyclopropanecarboxylate thiodicarb (II-6): (3 EZ,12 EZ)-3,7,9,13-tetramethyl-5,11-dioxa-2,8,14-trithia-4,7,9,12-tetraazapentadeca-3,12-diene-6,10-dione triflumezopyrim (mesoionic) (II-7): 3,4-dihydro-2,4-dioxo-1-(pyrimidin-5-ylmethyl)-3-(α,α,α-trifluoro-m-tolyl)-2H-pyrido[1,2-a]pyrimidin-1-ium-3-ide flupyradifurone (II-8): 4-[(6-chloro-3-pyridylmethyl)(2,2-difluoroethyl)amino]furan-2(5H)-one In a further embodiment, component II is selected the group of oxathiapiprolin (II-1); triadimenol (II-2); sulfoxaflor (II-3); methiocarb (II-4); thiodicarb (II-6); triflumezopyrim (Mesoionic) (II-7) and flupyradifurone (II-8).

In one embodiment, component II is selected from the group of oxathiapiprolin (II-1); triadimenol (II-2); sulfoxaflor (II-3); methiocarb (II-4) and triflumezopyrim (Mesoionic) (II-7).

In the following, the inventive compositions and their preferred uses are further described. In each case, according to the present invention, the use of the composition for controlling a particular pest, in particular phytopathogenic fungus is also meant to encompass the respective method for controlling the particular pest, in particular phytopathogenic fungi, wherein the fungi or the materials, plants, the soil or seed to be protected from attack are treated with an effective amount of a composition as defined herein.

According to a specific embodiment of the invention, only two active compounds as defined are present in the inventive compositions (herein also called "binary compositions"). The composition may, of course, contain any kind of additive or the like as detailed below in order to provide a formulation suitable for use in agriculture.

The weight ratio of component I to component II depends from the properties of the active substances used and is usually in the range of from 1:1000 to 1000:1, more particularly 1:500 to 500:1. The weight ratio of component I to component II may preferably be in the range of from 1:100 to 100:1, frequently in the range of from 1:50 to 50:1, preferably in the range of from 1:20 to 20:1, particularly preferably in the range of from 1:10 to 10:1, in particular in the range of from 1:3 to 3:1. It may also be preferable for the weight ratio to be in the range of from 1:2 to 2:1.

According to still further embodiments of the two-component compositions according to the invention, the weight ratio of component I to component II usually is in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to one embodiment, two-component compositions according to the invention may preferably have weight ratios of compound I versus compound II in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

The specific compositions of the invention are compiled in Table B1, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B1

Two-component compositions B1-1 to B1-248 comprising one component I and a component II, in particular binary compositions containing the respective component I and II as only active ingredients:

| composition | I | II |
|---|---|---|
| B1-1 | I-1 | II-1 |
| B1-2 | I-2 | II-1 |
| B1-3 | I-3 | II-1 |
| B1-4 | I-4 | II-1 |
| B1-5 | I-5 | II-1 |
| B1-6 | I-6 | II-1 |
| B1-7 | I-7 | II-1 |
| B1-8 | I-8 | II-1 |
| B1-9 | I-9 | II-1 |
| B1-10 | I-10 | II-1 |
| B1-11 | I-11 | II-1 |
| B1-12 | I-12 | II-1 |
| B1-13 | I-13 | II-1 |
| B1-14 | I-14 | II-1 |
| B1-15 | I-15 | II-1 |
| B1-16 | I-16 | II-1 |
| B1-17 | I-17 | II-1 |
| B1-18 | I-18 | II-1 |
| B1-19 | I-19 | II-1 |
| B1-20 | I-20 | II-1 |
| B1-21 | I-21 | II-1 |
| B1-22 | I-22 | II-1 |
| B1-23 | I-23 | II-1 |
| B1-24 | I-24 | II-1 |
| B1-25 | I-25 | II-1 |
| B1-26 | I-26 | II-1 |
| B1-27 | I-27 | II-1 |
| B1-28 | I-28 | II-1 |
| B1-29 | I-29 | II-1 |
| B1-30 | I-30 | II-1 |
| B1-31 | I-31 | II-1 |
| B1-32 | I-1 | II-2 |
| B1-33 | I-2 | II-2 |
| B1-34 | I-3 | II-2 |
| B1-35 | I-4 | II-2 |
| B1-36 | I-5 | II-2 |
| B1-37 | I-6 | II-2 |
| B1-38 | I-7 | II-2 |
| B1-39 | I-8 | II-2 |
| B1-40 | I-9 | II-2 |
| B1-41 | I-10 | II-2 |
| B1-42 | I-11 | II-2 |

TABLE B1-continued

Two-component compositions B1-1 to B1-248 comprising one component I and a component II, in particular binary compositions containing the respective component I and II as only active ingredients:

| composition | I | II |
|---|---|---|
| B1-43 | I-12 | II-2 |
| B1-44 | I-13 | II-2 |
| B1-45 | I-14 | II-2 |
| B1-46 | I-15 | II-2 |
| B1-47 | I-16 | II-2 |
| B1-48 | I-17 | II-2 |
| B1-49 | I-18 | II-2 |
| B1-50 | I-19 | II-2 |
| B1-51 | I-20 | II-2 |
| B1-52 | I-21 | II-2 |
| B1-53 | I-22 | II-2 |
| B1-54 | I-23 | II-2 |
| B1-55 | I-24 | II-2 |
| B1-56 | I-25 | II-2 |
| B1-57 | I-26 | II-2 |
| B1-58 | I-27 | II-2 |
| B1-59 | I-28 | II-2 |
| B1-60 | I-29 | II-2 |
| B1-61 | I-30 | II-2 |
| B1-62 | I-31 | II-2 |
| B1-63 | I-1 | II-3 |
| B1-64 | I-2 | II-3 |
| B1-65 | I-3 | II-3 |
| B1-66 | I-4 | II-3 |
| B1-67 | I-5 | II-3 |
| B1-68 | I-6 | II-3 |
| B1-69 | I-7 | II-3 |
| B1-70 | I-8 | II-3 |
| B1-71 | I-9 | II-3 |
| B1-72 | I-10 | II-3 |
| B1-73 | I-11 | II-3 |
| B1-74 | I-12 | II-3 |
| B1-75 | I-13 | II-3 |
| B1-76 | I-14 | II-3 |
| B1-77 | I-15 | II-3 |
| B1-78 | I-16 | II-3 |
| B1-79 | I-17 | II-3 |
| B1-80 | I-18 | II-3 |
| B1-81 | I-19 | II-3 |
| B1-82 | I-20 | II-3 |
| B1-83 | I-21 | II-3 |
| B1-84 | I-22 | II-3 |
| B1-85 | I-23 | II-3 |
| B1-86 | I-24 | II-3 |
| B1-87 | I-25 | II-3 |
| B1-88 | I-26 | II-3 |
| B1-89 | I-27 | II-3 |
| B1-90 | I-28 | II-3 |
| B1-91 | I-29 | II-3 |
| B1-92 | I-30 | II-3 |
| B1-93 | I-31 | II-3 |
| B1-94 | I-1 | II-4 |
| B1-95 | I-2 | II-4 |
| B1-96 | I-3 | II-4 |
| B1-97 | I-4 | II-4 |
| B1-98 | I-5 | II-4 |
| B1-99 | I-6 | II-4 |
| B1-100 | I-7 | II-4 |
| B1-101 | I-8 | II-4 |
| B1-102 | I-9 | II-4 |
| B1-103 | I-10 | II-4 |
| B1-104 | I-11 | II-4 |
| B1-105 | I-12 | II-4 |
| B1-106 | I-13 | II-4 |
| B1-107 | I-14 | II-4 |
| B1-108 | I-15 | II-4 |
| B1-109 | I-16 | II-4 |
| B1-110 | I-17 | II-4 |
| B1-111 | I-18 | II-4 |
| B1-112 | I-19 | II-4 |
| B1-113 | I-20 | II-4 |
| B1-114 | I-21 | II-4 |
| B1-115 | I-22 | II-4 |

TABLE B1-continued

Two-component compositions B1-1 to B1-248 comprising one component I and a component II, in particular binary compositions containing the respective component I and II as only active ingredients:

| composition | I | II |
|---|---|---|
| B1-116 | I-23 | II-4 |
| B1-117 | I-24 | II-4 |
| B1-118 | I-25 | II-4 |
| B1-119 | I-26 | II-4 |
| B1-120 | I-27 | II-4 |
| B1-121 | I-28 | II-4 |
| B1-122 | I-29 | II-4 |
| B1-123 | I-30 | II-4 |
| B1-124 | I-31 | II-4 |
| B1-125 | I-1 | II-5 |
| B1-126 | I-2 | II-5 |
| B1-127 | I-3 | II-5 |
| B1-128 | I-4 | II-5 |
| B1-129 | I-5 | II-5 |
| B1-130 | I-6 | II-5 |
| B1-131 | I-7 | II-5 |
| B1-132 | I-8 | II-5 |
| B1-133 | I-9 | II-5 |
| B1-134 | I-10 | II-5 |
| B1-135 | I-11 | II-5 |
| B1-136 | I-12 | II-5 |
| B1-137 | I-13 | II-5 |
| B1-138 | I-14 | II-5 |
| B1-139 | I-15 | II-5 |
| B1-140 | I-16 | II-5 |
| B1-141 | I-17 | II-5 |
| B1-142 | I-18 | II-5 |
| B1-143 | I-19 | II-5 |
| B1-144 | I-20 | II-5 |
| B1-145 | I-21 | II-5 |
| B1-146 | I-22 | II-5 |
| B1-147 | I-23 | II-5 |
| B1-148 | I-24 | II-5 |
| B1-149 | I-25 | II-5 |
| B1-150 | I-26 | II-5 |
| B1-151 | I-27 | II-5 |
| B1-152 | I-28 | II-5 |
| B1-153 | I-29 | II-5 |
| B1-154 | I-30 | II-5 |
| B1-155 | I-31 | II-5 |
| B1-156 | I-1 | II-6 |
| B1-157 | I-2 | II-6 |
| B1-158 | I-3 | II-6 |
| B1-159 | I-4 | II-6 |
| B1-160 | I-5 | II-6 |
| B1-161 | I-6 | II-6 |
| B1-162 | I-7 | II-6 |
| B1-163 | I-8 | II-6 |
| B1-164 | I-9 | II-6 |
| B1-165 | I-10 | II-6 |
| B1-166 | I-11 | II-6 |
| B1-167 | I-12 | II-6 |
| B1-168 | I-13 | II-6 |
| B1-169 | I-14 | II-6 |
| B1-170 | I-15 | II-6 |
| B1-171 | I-16 | II-6 |
| B1-172 | I-17 | II-6 |
| B1-173 | I-18 | II-6 |
| B1-174 | I-19 | II-6 |
| B1-175 | I-20 | II-6 |
| B1-176 | I-21 | II-6 |
| B1-177 | I-22 | II-6 |
| B1-178 | I-23 | II-6 |
| B1-179 | I-24 | II-6 |
| B1-180 | I-25 | II-6 |
| B1-181 | I-26 | II-6 |
| B1-182 | I-27 | II-6 |
| B1-183 | I-28 | II-6 |
| B1-184 | I-29 | II-6 |
| B1-185 | I-30 | II-6 |
| B1-186 | I-31 | II-6 |
| B1-187 | I-1 | II-7 |
| B1-188 | I-2 | II-7 |
| B1-189 | I-3 | II-7 |
| B1-190 | I-4 | II-7 |
| B1-191 | I-5 | II-7 |
| B1-192 | I-6 | II-7 |
| B1-193 | I-7 | II-7 |
| B1-194 | I-8 | II-7 |
| B1-195 | I-9 | II-7 |
| B1-196 | I-10 | II-7 |
| B1-197 | I-11 | II-7 |
| B1-198 | I-12 | II-7 |
| B1-199 | I-13 | II-7 |
| B1-200 | I-14 | II-7 |
| B1-201 | I-15 | II-7 |
| B1-202 | I-16 | II-7 |
| B1-203 | I-17 | II-7 |
| B1-204 | I-18 | II-7 |
| B1-205 | I-19 | II-7 |
| B1-206 | I-20 | II-7 |
| B1-207 | I-21 | II-7 |
| B1-208 | I-22 | II-7 |
| B1-209 | I-23 | II-7 |
| B1-210 | I-24 | II-7 |
| B1-211 | I-25 | II-7 |
| B1-212 | I-26 | II-7 |
| B1-213 | I-27 | II-7 |
| B1-214 | I-28 | II-7 |
| B1-215 | I-29 | II-7 |
| B1-216 | I-30 | II-7 |
| B1-217 | I-31 | II-7 |
| B1-218 | I-1 | II-8 |
| B1-219 | I-2 | II-8 |
| B1-220 | I-3 | II-8 |
| B1-221 | I-4 | II-8 |
| B1-222 | I-5 | II-8 |
| B1-223 | I-6 | II-8 |
| B1-224 | I-7 | II-8 |
| B1-225 | I-8 | II-8 |
| B1-226 | I-9 | II-8 |
| B1-227 | I-10 | II-8 |
| B1-228 | I-11 | II-8 |
| B1-229 | I-12 | II-8 |
| B1-230 | I-13 | II-8 |
| B1-231 | I-14 | II-8 |
| B1-232 | I-15 | II-8 |
| B1-233 | I-16 | II-8 |
| B1-234 | I-17 | II-8 |
| B1-235 | I-18 | II-8 |
| B1-236 | I-19 | II-8 |
| B1-237 | I-20 | II-8 |
| B1-238 | I-21 | II-8 |
| B1-239 | I-22 | II-8 |
| B1-240 | I-23 | II-8 |
| B1-241 | I-24 | II-8 |
| B1-242 | I-25 | II-8 |
| B1-243 | I-26 | II-8 |
| B1-244 | I-27 | II-8 |
| B1-245 | I-28 | II-8 |
| B1-246 | I-29 | II-8 |
| B1-247 | I-30 | II-8 |
| B1-248 | I-31 | II-8 |

I = component I selected from compounds I-1 to I-31
II = oxathiapiprolin (II-1); triadimenol (II-2); sulfoxaflor (II-3); methiocarb (II-4); cypermethrin (II-5); thiodicarb (II-6); triflumezopyrim (mesoionic) (II-7) and flupyradifurone (II-8).

The weight ratio of component I to component II in the compositions B1-1 to B1-248 depends from the properties of the active substances used and is usually in the range of from 1:1000 to 1000:1, more particularly 1:500 to 500:1. The weight ratio of component I to component II in the compositions B1-1 to B1-248 may preferably be in the range of from 1:100 to 100:1, frequently in the range of from 1:50 to 50:1, preferably in the range of from 1:20 to 20:1, particularly preferably in the range of from 1:10 to 10:1, in particular in the range of from 1:3 to 3:1. It may also be preferable for the weight ratio to be in the range of from 1:2 to 2:1.

According to still further embodiments of the compositions B1-1 to B1-248 according to the invention, the weight ratio of component I to component II usually is in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to one further embodiment, the compositions B1-1 to B1-248 according to the invention may preferably have weight ratios of component I versus compound II in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

One embodiment of the invention relates to any one of compositions B1-1 to B1-248 wherein the weight ratio of component I to component II is from 1000:1 to 1:1000.

One further embodiment of the invention relates to any one of compositions B1-1 to B1-248 wherein the weight ratio of component I to component II is from 500:1 to 1:500.

One further embodiment of the invention relates to any one of compositions B1-1 to B1-248 wherein the weight ratio of component I to component II is from 100:1 to 1:100.

One further embodiment of the invention relates to any one of compositions B1-1 to B1-248 wherein the weight ratio of component I to component II is from 1:100 to 100:1.

One further embodiment of the invention relates to any one of compositions B1-1 to B1-248 wherein the weight ratio of component I to component II is from 1:50 to 50:1.

One further embodiment of the invention relates to any one of compositions B1-1 to B1-248 wherein the weight ratio of component I to component II is from 1:20 to 20:1.

One further embodiment of the invention relates to any one of compositions B1-1 to B1-248 wherein the weight ratio of component I to component II is from 1:10 to 10:1.

One further embodiment of the invention relates to any one of compositions B1-1 to B1-248 wherein the weight ratio of component I to component II is from 1:3 to 3:1.

One further embodiment of the invention relates to any one of compositions B1-1 to B1-248 wherein the weight ratio of component I to component II is from 1:2 to 2:1.

One further embodiment of the invention relates to any one of compositions B1-1 to B1-248 wherein the weight ratio of component I to component II is from 1000:1 to 1:1.

One further embodiment of the invention relates to any one of compositions B1-1 to B1-248 wherein the weight ratio of component I to component II is from 100:1 to 1:1.

One further embodiment of the invention relates to any one of compositions B1-1 to B1-248 wherein the weight ratio of component I to component II is from 50:1 to 1:1.

One further embodiment of the invention relates to any one of compositions B1-1 to B1-248 wherein the weight ratio of component I to component II is from 20:1 to 1:1.

One further embodiment of the invention relates to any one of compositions B1-1 to B1-248 wherein the weight ratio of component I to component II is from 10:1 to 1:1.

One further embodiment of the invention relates to any one of compositions B1-1 to B1-248 wherein the weight ratio of component I to component II is from 4:1 to 1:1.

One further embodiment of the invention relates to any one of compositions B1-1 to B1-248 wherein the weight ratio of component I to component II is from 2:1 to 1:1.

One further embodiment of the invention relates to any one of compositions B1-1 to B1-248 wherein the weight ratio of component I to component II is from 1:1 to 1000.

One further embodiment of the invention relates to any one of compositions B1-1 to B1-248 wherein the weight ratio of component I to component II is from 1:1 to 1:100.

One further embodiment of the invention relates to any one of compositions B1-1 to B1-248 wherein the weight ratio of component I to component II is from 1:1 to 1:50.

One further embodiment of the invention relates to any one of compositions B1-1 to B1-248 wherein the weight ratio of component I to component II is from 1:1 to 1:20.

One further embodiment of the invention relates to any one of compositions B1-1 to B1-248 wherein the weight ratio of component I to component II is from 1:1 to 1:10.

One further embodiment of the invention relates to any one of compositions B1-1 to B1-248 wherein the weight ratio of component I to component II is from 1:1 to 1:4.

One further embodiment of the invention relates to any one of compositions B1-1 to B1-248 wherein the weight ratio of component I to component II is from 1:1 to 1:2.

As detailed above, the components I contain chirality centers and may, therefore, be present as racemic mixtures, as pure enantiomers or in the two enantiomers of one component I may be present in any ratio (S):(R).

According to particular embodiments of the invention, the respective component I is present as (S) enantiomer. According to particular embodiments of the invention, the respective component I is present as (R) enantiomer. According to one specific aspect, these are binary compositions which each only contain these two components as active compounds.

The compositions according to the invention are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e. g. conifers; and on the plant propagation material, such as seeds, and the crop material of these plants.

Preferably the inventive compositions are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the inventive combination of pesticides I and pesticides II and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as 6-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the CryIAc toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The inventive compositions are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.) on corn (e. g. *D. maydis*), cereals (e. g. *B. sorokiniana*: spot blotch), rice (e. g. *B. oryzae*) and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce;

*Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn, rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*), soft fruits, potatoes (e. g. *C. coccodes* black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; *Esca* (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohllum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. glycines now syn. *F. virguliforme*) and *F. tucumaniae* and *F. brasillense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*, Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiensis* black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meiborniae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae*

(root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodophora brassicae* (club root) on cabbage, rape, radish and other plants; *Plasmopara* spp., e. g. *P. v/t/co/a* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporlla herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, and asparagus (e. g. *P. asparagi*); *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckerii*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

In particular, compositions of the present invention are effective against plant pathogens in speciality crops such as vine, fruits, hop, vegetables and tobacco—see above list.

The inventive compositions are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystsis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

Plant propagation materials may be treated with the compositions of the invention prophylactically either at or before planting or transplanting.

The invention also relates to agrochemical compositions comprising an auxiliary and at least one compound I and at least one pesticide II according to the invention.

An agrochemical composition comprises a fungicidally effective amount of a compound I and a pesticide II. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I and pesticides II, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methylpyrrolidone, fatty acid dimethylamides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkyliso-thiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are (wherein active substances denote at least one compound I and one compound II):

i) Water-Soluble Concentrates (SL, LS)

10-60 wt % active substances and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % active substances and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % active substances and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % active substances and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % active substances are comminuted with addition of 2-10 wt % dispersants and wetting agents (e. g. sodium lignosulfonate and alcohol ethoxylate), 0.1-2 wt % thickener (e. g. xanthan gum) and ad water ad 100 wt % to give a fine active substance suspension. Dilution with water gives a stable suspension of the active substance. For FS type composition up to 40 wt % binder (e. g. polyvinyl alcohol) is added.

vi) Water-dispersible granules and water-soluble granules (WG, SG)

50-80 wt % active substances are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % active substances are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % active substances are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

iv) Microemulsion (ME)

5-20 wt % active substances are added to 5-30 wt % organic solvent blend (e. g. fatty acid dimethylamide and cyclohexanone), 10-25 wt % surfactant blend (e. g. alcohol ethoxylate and arylphenol ethoxylate), and water ad 100 wt %. This mixture is stirred for 1 h to produce spontaneously a thermodynamically stable microemulsion.

iv) Microcapsules (CS)

An oil phase comprising 5-50 wt % active substances, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanate) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

ix) Dustable Powders (DP, DS)

1-10 wt % active substances are ground finely and mixed intimately with solid carrier (e. g. finely divided kaolin) ad 100 wt %.

x) Granules (GR, FG)

0.5-30 wt % active substances are ground finely and associated with solid carrier (e. g. silicate) ad 100 wt %. Granulation is achieved by extrusion, spray-drying or fluidized bed.

xi) Ultra-Low Volume Liquids (UL)

1-50 wt % active substances are dissolved in organic solvent (e. g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substances. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying or treating compound I and compound II and compositions thereof, respectively, onto plant propagation material, especially seeds include dressing, coating, pelleting, dusting, and soaking as well as in-furrow application methods. Preferably, compound I and pesticide II or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.

g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

In the compositions, the compound ratios are advantageously chosen so as to produce a synergistic effect.

The term "synergistic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

The active compounds, separately or jointly, are prepared as a stock solution comprising 25 mg of active compound which is made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture is then made up to 100 ml with water. This stock solution is diluted with the solvent/emulsifier/water mixture described to give the concentration of active compound stated below.

The visually determined percentages of infected leaf areas are converted into efficacies in % of the untreated control. The efficacy (E) is calculated as follows using Abbots formula:

$$E=(1-\alpha/\beta)\cdot 100$$

α corresponds to the fungicidal infection of the treated plants in % and
β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

$$E=x+y-x\cdot y/100 \qquad \text{Colby's formula:}$$

E expected efficacy, expressed in % of the untreated control, when using the mixture of the active compounds A and B at the concentrations a and b
x efficacy, expressed in % of the untreated control, when using the active compound A at the concentration a
y efficacy, expressed in % of the untreated control, when using the active compound B at the concentration b.

The fungicidal action of the compositions according to the invention can be shown by the tests described below.

Microtest

The active compounds were formulated separately as a stock solution having a concentration of 10000 ppm in dimethyl sulfoxide. The product sulfoxaflor was used as a commercial finished formulation and diluted with water to the stated concentration of the active compound.

M1 Activity Against the Late Blight Pathogen *Phytophthora infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

M2 Activity Against the Grey Mold *Botrytis cinerea* in the Microtiterplate Test (*Botrci*)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

M3 Activity Against Rice Blast *Pyricularia oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation.

M4 Activity Against Leaf Blotch on Wheat Caused by *Septoria tritici*(Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

M5 Activity Against Early Blight Caused by *Alternaria solani* (Alteso)

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

M6 Activity Against Wheat Leaf Spots Caused by *Leptosphaeria nodorum* (Leptno)

The stock solutions were mixed according to the ratio, pipetted onto a micro titer plate (MTP) and diluted with water to the stated concentrations. A spore suspension of *Leptosphaeria nodorum* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies.

An efficacy of 0 means that the growth level of the pathogens corresponds to that of the untreated control; an efficacy of 100 means that the pathogens were not growing.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Results:

M1 Phytin

| Active compound/ active mixture | Concentration (ppm) | Mixture | Observed efficacy | Calculated efficacy according to Colby (%) | Synergism (%) |
|---|---|---|---|---|---|
| I-3* | 0.063 | — | 12 | | |
| Methiocarb (II-4) | 63 | — | 51 | | |
| I-3* Methiocarb (II-4) | 0.063 63 | 1:1000 | 75 | 57 | 18 |

M2 Botrci

| Active compound/ active mixture | Concentration (ppm) | Mixture | Observed efficacy | Calculated efficacy according to Colby (%) | Synergism (%) |
|---|---|---|---|---|---|
| I-3* | 0.063 | — | 42 | | |
| Oxathiapiprolin (II-1) | 63 16 | — | 23 4 | | |
| Triadimenol (II-2) | 4 | — | 39 | | |
| I-3* Oxathiapiprolin (II-1) | 0.063 16 | 1:250 | 68 | 44 | 24 |
| I-3* Oxathiapiprolin (II-1) | 0.063 63 | 1:1000 | 73 | 55 | 18 |
| I-3* Triadimenol (II-2) | 0.063 4 | 1:63 | 91 | 65 | 26 |

M3 Pyrior

| Active compound/ active mixture | Concentration (ppm) | Mixture | Observed efficacy | Calculated efficacy according to Colby (%) | Synergism (%) |
|---|---|---|---|---|---|
| I-3* | 0.25 | — | 10 | | |
| Methiocarb (II-4) | 63 | — | 36 | | |
| I-3* Methiocarb (II-4) | 0.25 63 | 1:250 | 100 | 43 | 57 |

M4 Septtr

| Active compound/ active mixture | Concentration (ppm) | Mixture | Observed efficacy | Calculated efficacy according to Colby (%) | Synergism (%) |
|---|---|---|---|---|---|
| I-3* | 0.00025 | — | 28 | | |
| Methiocarb (II-4) | 0.063 | — | 6 | | |
| I-3* Methiocarb (II-4) | 0.00025 0.063 | 1:250 | 60 | 32 | 28 |

M5 Alteso

| Active compound/ active mixture | Concentration (ppm) | Mixture | Observed efficacy | Calculated efficacy according to Colby (%) | Synergism (%) |
|---|---|---|---|---|---|
| I-3* | 0.001 | — | 9 | | |
| Triflumezopyrim (II-7) | 0.25 | — | 36 | | |
| I-3* Triflumezopyrim (II-7) | 0.001 0.25 | 1:250 | 33 | 15 | 18 |

M6 Leptno

| Active compound/ active mixture | Concentration (ppm) | Mixture | Observed efficacy | Calculated efficacy according to Colby (%) | Synergism (%) |
|---|---|---|---|---|---|
| I-3* | 0.016 | — | 35 | | |
| Sulfoxaflor (II-3) | 16 | — | 0 | | |
| I-3* Sulfoxaflor (II-3) | 0.016 16 | 1:1000 | 78 | 35 | 43 |

*I-3: 2-[4-(4-chlorophenoxy)-2-(trifluoromethyl)phenyl]-1-(1,2,4-triazol-1-yl)propan-2-ol

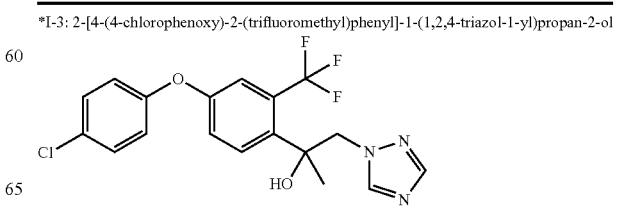

The invention claimed is:
1. A composition comprising,
1) as component I a compound selected from:
compound I-1 2-[2-chloro-4-(4-chlorophenoxy)phenyl]-1-(1,2,4-triazol-1-yl)pent-3-yn-2-ol;
compound I-2 1-[2-chloro-4-(4-chlorophenoxy)phenyl]-1-cyclopropyl-2-(1,2,4-triazol-1-yl)ethanol;
compound I-3 2-[4-(4-chlorophenoxy)-2-(trifluoromethyl)phenyl]-1-(1,2,4-triazol-1-yl)propan-2-ol;
compound I-4 1-[4-(4-chlorophenoxy)-2-(trifluoromethyl)phenyl]-1-cyclopropyl-2-(1,2,4-triazol-1-yl)ethanol;
compound I-5 2-[4-(4-chlorophenoxy)-2-(trifluoromethyl)phenyl]-3-methyl-1-(1,2,4-triazol-1-yl)butan-2-ol;
compound I-6 1-[2-[2-chloro-4-(4-chlorophenoxy)phenyl]-2-methoxy-pent-3-ynyl]-1,2,4-triazole;
compound I-7 2-[4-(4-chlorophenoxy)-2-(trifluoromethyl)phenyl]-1-(1,2,4-triazol-1-yl)butan-2-ol;
compound I-8 1-[2-[2-chloro-4-(4-chlorophenoxy)phenyl]-2-cyclopropyl-2-methoxy-ethyl]-1,2,4-triazole;
compound I-9 1-[2-[4-(4-chlorophenoxy)-2-(trifluoromethyl)phenyl]-2-methoxy-propyl]-1,2,4-triazole;
compound I-10 2-[2-chloro-4-(4-chlorophenoxy)phenyl]-3,3-dimethyl-1-(1,2,4-triazol-1-yl)butan-2-ol,
compound I-11 1-[2-[4-(4-chlorophenoxy)-2-(trifluoromethyl)phenyl]-2-cyclopropyl-2-methoxy-ethyl]-1,2,4-triazole;
compound I-12 1-[2-[2-chloro-4-(4-chlorophenoxy)phenyl]-2-methoxy-3,3-dimethyl-butyl]-1,2,4-triazole;
compound I-13 1-[2-[4-(4-chlorophenoxy)-2-(trifluoromethyl)phenyl]-2-methoxy-butyl]1,2,4-triazole;
compound I-14 2-[4-(4-chlorophenoxy)-2-(trifluoromethyl)phenyl]-1-(1,2,4-triazol-1-yl)pent-3-yn-2-ol;
compound I-15 1-[2-[4-(4-chlorophenoxy)-2-(trifluoromethyl)phenyl]-2-methoxy-pent-3-ynyl]-1,2,4-triazole;
compound I-16 2-[4-(4-chlorophenoxy)-2-(trifluoromethyl)phenyl]-1-(1,2,4-triazol-1-yl)but-3-yn-2-ol;
compound I-17 2-[2-chloro-4-(4-chlorophenoxy)phenyl]-1-(1,2,4-triazol-1-yl)propan-2-ol;
compound I-18 2-[2-chloro-4-(4-fluorophenoxy)phenyl]-1-(1,2,4-triazol-1-yl)propan-2-ol;
compound I-19 2-[2-chloro-4-(4-chlorophenoxy)phenyl]-3-methyl-1-(1,2,4-triazol-1-yl)butan-2-ol;
compound I-20 1-[2-[2-chloro-4-(4-chlorophenoxy)phenyl]-2-methoxy-propyl]-1,2,4-triazole;
compound I-21 1-[2-[2-chloro-4-(4-chlorophenoxy)phenyl]-2-methoxy-butyl]-1,2,4-triazole;
compound I-22 1-[2-[2-chloro-4-(4-chlorophenoxy)phenyl]-2-methoxy-pentyl]-1,2,4-triazole;
compound I-23 2-[2-chloro-4-(4-chlorophenoxy)phenyl]-1,1,1-trifluoro-3-(1,2,4-triazol-1-yl)propan-2-ol;
compound I-24 2-[2-chloro-4-(4-chlorophenoxy)phenyl]-3-fluoro-1-(1,2,4-triazol-1-yl)butan-2-ol hydrochloride;
compound I-25 2-[2-chloro-4-(4-chlorophenoxy)phenyl]-1-(1,2,4-triazol-1-yl)pent-4-yn-2-ol;
compound I-26 2-[2-chloro-4-(4-chlorophenoxy)phenyl]-1-methoxy-3-(1,2,4-triazol-1-yl)propan-2-ol;
compound I-27 2-[2-chloro-4-(4-fluorophenoxy)phenyl]-1-methoxy-3-(1,2,4-triazol-1-yl)propan-2-ol;
compound I-28 2-[4-(4-chlorophenoxy)-2-(trifluoromethyl)phenyl]-1-(1,2,4-triazol-1-yl)pentan-2-ol;
compound I-29 and 2-[4-(4-fluorophenoxy)-2-(trifluoromethyl)phenyl]-1-(1,2,4-triazol-1-yl)propan-2-ol;
compound I-30 2-[2-chloro-4-(4-chlorophenoxy)phenyl]-1-(1,2,4-triazol-1-yl)butan-2-ol; and
compound I-31 2-[2-chloro-4-(4-chlorophenoxy)phenyl]-1-(1,2,4-triazol-1-yl)pentan-2-ol;
and
2) as component II a compound selected from the group of sulfoxaflor (II-3); and triflumezopyrim (II-7).
2. The composition of claim 1, wherein component II is sulfoxaflor (II-3).
3. The composition of claim 1, wherein component II is triflumezopyrim (II-7).
4. The composition of claim 1, wherein the compound I and the component II are present in a synergistically effective amount.
5. The composition of claim 1, wherein component I and component II are present in a total weight ratio of from 100:1 to 1:100.
6. The composition of claim 1, wherein component I is selected from the compounds I-1, I-3, I-4, I-5, I-13, I-17, I-18 and I-19.
7. The composition of claim 1, wherein component I is selected from the compounds I-3, I-4 and I-5.
8. The composition of claim 1, further comprising an agrochemical auxiliary.
9. A method for combating phytopathogenic fungi, comprising treating the fungi or the materials, plants, the soil or seeds to be protected against fungal attack with an effective amount of the composition of claim 1.
10. The method of claim 9, wherein component II is sulfoxaflor (II-3).
11. The method of claim 9, wherein component II is triflumezopyrim (II-7).
12. The method of claim 9, wherein component I is selected from the compounds I-1, I-3, I-4, I-5, I-13, I-17, I-18 and I-19.
13. A plant propagation material, coated with the components and II of the composition of claim 1, in an amount of from 0.1 to 10 kg active substances per 100 kg of seed.

* * * * *